(12) United States Patent
Bourne

(10) Patent No.: US 9,066,669 B2
(45) Date of Patent: Jun. 30, 2015

(54) APPARATUS AND METHODS FOR FITTING ATTACHMENTS

(71) Applicant: Duncan Bourne, Surrey (GB)

(72) Inventor: Duncan Bourne, Surrey (GB)

(73) Assignee: Elekta AB (publ), Stockholm (SE)

( * ) Notice: Subject to any disclaimer, the term of this patent is extended or adjusted under 35 U.S.C. 154(b) by 31 days.

(21) Appl. No.: 13/646,938

(22) Filed: Oct. 8, 2012

(65) Prior Publication Data

US 2014/0096321 A1   Apr. 10, 2014

(51) Int. Cl.
*A61B 6/04* (2006.01)
*A61B 6/06* (2006.01)
*A61N 5/10* (2006.01)
*A61B 6/00* (2006.01)

(52) U.S. Cl.
CPC ......... *A61B 6/0407* (2013.01); *Y10T 29/49826* (2015.01); *A61B 6/0442* (2013.01); *A61B 6/0457* (2013.01); *A61B 6/06* (2013.01); *A61B 6/4411* (2013.01); *A61N 5/1081* (2013.01)

(58) Field of Classification Search
CPC .... A61B 6/407; A61B 6/0442; A61B 6/0457; A61B 6/06; A61B 6/4411; A61N 5/1081
USPC ....................................... 5/601; 600/441, 436
See application file for complete search history.

(56) References Cited

U.S. PATENT DOCUMENTS

| | | | |
|---|---|---|---|
| 5,519,223 A | 5/1996 | Hug | |
| 6,027,247 A | 2/2000 | Tachi et al. | |
| 6,441,377 B1 | 8/2002 | Hug et al. | |
| 6,590,214 B1 | 7/2003 | Karmalawy | |
| 7,014,361 B1 | 3/2006 | Ein-Gal | |
| 7,898,192 B2 | 3/2011 | Maltz | |
| 8,160,205 B2 | 4/2012 | Saracen | |
| 8,173,966 B2 | 5/2012 | Caruba | |
| 2005/0080331 A1* | 4/2005 | Burckhardt et al. | 600/411 |
| 2006/0020201 A1 | 1/2006 | Caruba | |

FOREIGN PATENT DOCUMENTS

| | | |
|---|---|---|
| WO | 03107038 A1 | 12/2003 |
| WO | 2008063303 A2 | 5/2008 |
| WO | 2011009616 A1 | 1/2011 |

OTHER PUBLICATIONS

European Search Report in Corresponding Application No. 13185964.7. Jan. 23, 2014.

* cited by examiner

*Primary Examiner* — Peter M Cuomo
*Assistant Examiner* — Brittany Wilson
(74) *Attorney, Agent, or Firm* — Westman, Champlin & Koehler, P.A.; Z. Peter Sawicki

(57) ABSTRACT

Embodiments of the present invention provide a system and a method for attaching peripheral devices (such as collimators and electron applicators) to a system such as a radiotherapy system or radiography system. By re-using the lifting mechanism of the patient support to lift the peripheral device vertically, the invention reduces the need for heavy manual lifting.

7 Claims, 4 Drawing Sheets

APPARATUS AND METHODS FOR FITTING ATTACHMENTS

TECHNICAL FIELD

The present invention relates to apparatus and methods for fitting attachments to a radiotherapy or radiography system, as well as apparatus and methods for manipulating such attachments.

BACKGROUND

Different types of radiotherapy often involve the use of different attachments or add-on devices on the radiation head, such as a multi-leaf collimator or an electron applicator. Such add-on devices are typically attached to the radiation head so that they move with the source of radiation, and continue to have the desired effect on the radiation beam regardless of the motion or position of the radiation head. Further, add-on devices may be attached to other parts of the gantry, to provide filters for imaging devices, or light sources, etc.

However, changing these add-on devices can be difficult, as they are generally heavy and difficult to lift, sometimes requiring two or more people to attach them correctly. It also takes significant amounts of time, during which the system cannot be used to treat patients and the staff required to put the attachment in place are taken away from their other duties.

SUMMARY OF INVENTION

According to a first aspect of the present invention, there is provided a method of attaching an attachment to a radiotherapy or radiography system, the system comprising a rotatable gantry having a connection point, and a patient support for supporting a patient, the patient support comprising an engagement mechanism, the method comprising: bringing the engagement mechanism into engagement with the attachment; raising the patient support and thus also the attachment; positioning the connection point beneath the attachment; lowering the patient support and engaging the attachment with the connection point; and disengaging the engagement mechanism from the attachment.

A second aspect of the invention provides an apparatus, comprising: a rotatable gantry; a connection point mounted on the rotatable gantry; an attachment for attachment to the connection point; a patient support for supporting a patient, comprising an engagement mechanism for engagement with the attachment; and a control apparatus for controlling at least the patient support and the rotatable gantry, the control apparatus arranged to: bring the engagement mechanism into engagement with the attachment; raise the patient support and thus also the attachment; position the connection point beneath the attachment; lower the patient support and engage the attachment with the connection point; and disengage the engagement mechanism from the attachment.

A third aspect of the invention provides a method of controlling a patient support, the patient support comprising a surface for supporting a patient, one or more support mechanisms for manipulating the position and/or orientation of the surface, and an engagement mechanism for engaging with an object, the method comprising: controlling the one or more support mechanisms to bring the engagement mechanism into engagement with the object; and manipulating the position and/or orientation of the object through control of the one or more support mechanisms.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1A:
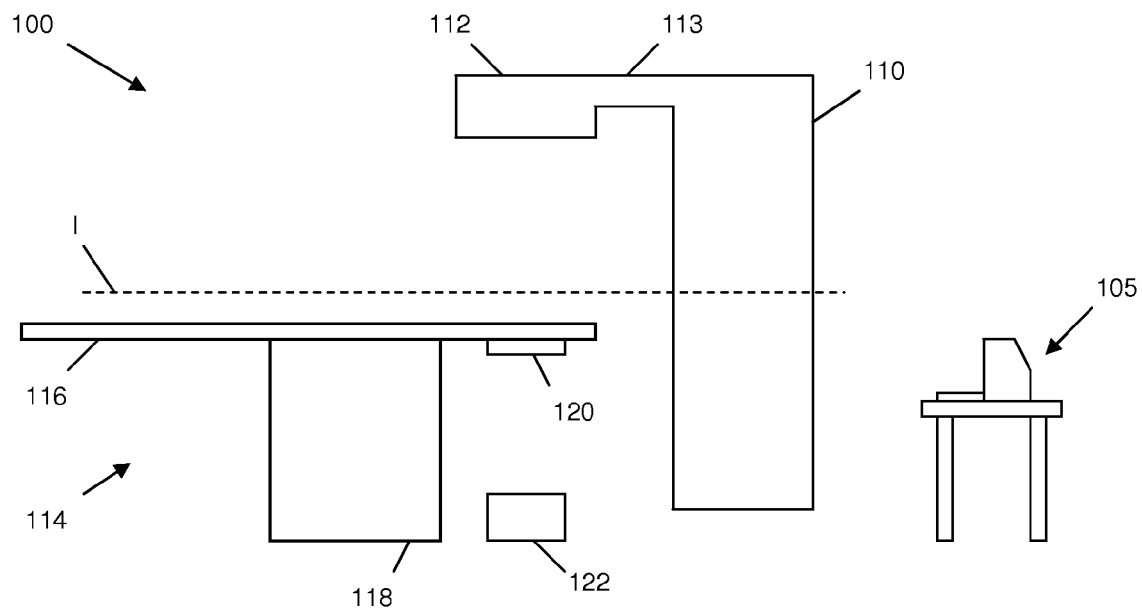
FIGS. 1A to 1G show the sequential steps in a method according to embodiments of the present invention of attaching an add-on device to a radiation head.

FIGS. 1A to 1G show the different stages in a method of automatically attaching attachments to a radiotherapy system 100 according to embodiments of the present invention. FIG. 1A can be used to illustrate the radiotherapy system 100.

The system comprises a gantry 110 which is able to rotate around an axis I. A radiation head 112 is mounted on the gantry 110, and comprises a source of radiation (not illustrated) directed inwards towards the axis of rotation I. In an embodiment, the source comprises a linear accelerator, or linac, arranged to accelerate charged particles (such as electrons) to relativistic speeds and energies in the megavoltage (MV) range. The charged particles may then be used to treat the patient directly, typically for targets on or near the surface of the patient, or fired towards a high-density target (e.g. tungsten) to generate secondary radiation via mechanisms such as Bremsstrahlung radiation. The secondary radiation so generated includes x-rays up to and including the energy of the charged particle. The therapeutic radiation generated by the source is collimated into a beam having a particular shape (cone-shaped and fan-shaped beams are well known but other shapes are possible) by primary collimators.

In the illustrated embodiment, the radiation head is mounted on the gantry 110 via an arm 113, and so projects away from the gantry 110 in a direction substantially parallel to the rotation axis I. Further devices may be mounted on the gantry 110 as required, and typically these will also be mounted via arms which project away from the gantry 110 some distance parallel to the axis of rotation. For example, a common arrangement is to position a radiation detector such as a portal imager diametrically opposite the radiation head 112. The combination of a radiation head and a radiation detector is known as a "C-arm". In this way, the radiation beam generated by the radiation head 112 can be imaged after it has passed through the patient.

A patient support 114 is located on or near the rotation axis I, and comprises a patient bed 116 (i.e. a support on which the patient can rest during treatment) and a support mechanism 118 for supporting and positioning the bed 116. In embodiments of the present invention, the support mechanism 118 comprises at least a mechanism for raising and lowering the bed 116 vertically (i.e. up and down the page in FIG. 1A). In further embodiments, the support mechanism 118 allows rotation of the bed 116 around a vertical axis. In yet further embodiments, the support mechanism 118 may allow the position and orientation of the bed 116 to be altered in up to six degrees of freedom (e.g. three degrees of translational freedom and three degrees of rotational freedom).

A control apparatus 105 (e.g. a computer or similar device) can be used to control operation of the system, such as the positions and orientations of the patient support 114 and the gantry 110, as well as the engagement mechanism(s) to be described hereinafter. The control apparatus 105 is illustrated in FIG. 1A, but omitted from subsequent Figures for clarity.

In use, the therapeutic beam is directed generally towards the rotation axis of the gantry 110. A patient is positioned on the bed 116 such that the target for treatment lies on or near the intersection of the radiation beam and the rotational axis (known as the isocentre). Rotation of the gantry 110 during treatment causes rotation of the radiation head 112 and thus the beam is directed towards the target from multiple directions. The target remains in the treatment beam for most (or all) of the time and thus radiation dose accumulates to a relatively high level there. The surrounding healthy tissue also lies within the radiation beam but only for a limited period of time before the gantry rotates and the beam passes through a different part of the patient. Radiation dose in the healthy tissue is therefore kept at a relatively low level.

In order to minimize further the level of radiation dose in surrounding healthy tissue, radiotherapy systems usually employ one or more secondary collimators to shape the radiation beam as required. For example, the cross section of the beam may be altered to match the cross section of the target within the patient (although it should be noted that treatment planning is complex and thus alternative shapes can be used). One well-known collimator is the multi-leaf collimator, named due to its use of a bank of leaves which project into and out of the radiation beam in order to block and shape the radiation. However, other collimators are known. In use, the collimator is attached to the radiation head 112 so that it acts on the radiation beam at all positions and all angles of rotation.

During electron therapy (i.e. when the radiation head 112 is controlled to emit therapeutic electrons), electron applicators can be used to shape the beam of electrons to conform to a desired profile (for example to conform to the shape of a target on the patient). Electron applicators may comprise a number of holders into which shields can be selectively added to provide a collimating effect. For example, the shields may have a cut-out area defining a particular shape through which the electron beam can pass, and be manufactured from an element with high atomic number (such as tungsten or lead) to otherwise block the radiation.

Further devices can be fitted to the gantry 110 as required. For example, light sources, X-ray detectors or sources, laser scanners, ultrasound or infrared sensors for patient motion or proximity measurements, video cameras or other sensors/detectors/beam collimation means may all be attached to the radiation head 112 or to an arm extending from the gantry 110.

All of these attachments need to be fitted to the system 100 in order to perform their function but, as explained above, they can be heavy and awkward to lift. According to embodiments of the present invention, the patient support 114 is manipulated in order to bring the add-on device into engagement with the system 100, without requiring any heavy manual lifting.

The patient support 114 therefore further comprises an engagement mechanism 120 for engaging with an attachment 122. In the illustrated embodiment, the attachment 122 is for the radiation head 112, but it will be apparent that the attachment could be for another connection point on the gantry (for example, a connection point provided on an arm extending from the gantry 110). In the illustrated embodiment, the engagement mechanism is positioned on the underside of the bed 116 (at the foot or head of the bed—see below). However, in alternative arrangements the mechanism may be mounted on an upper part of the support mechanism 118. In either case, adjustment of the support mechanism 118—which would conventionally be used only to move the bed 116—causes consequential movement of the engagement mechanism 120.

The engagement mechanism 120 may take any form suitable for lifting and positioning heavy objects (such as the attachment 122). For example, the mechanism may comprise one or more clamps for gripping a part or all of the attachment 122. The attachment 122 itself may be adapted to engage with the mechanism 120. For example, the engagement mechanism 120 (e.g. a clamp) may take a particular non-symmetrical shape and engage with a correspondingly shaped feature provided on the attachment 122. In this way, the mechanism and the attachment can become engaged in a reproducible orientation. Alternative mechanisms will be apparent to those skilled in the art.

The engagement mechanism 120 may be manufactured from material which is substantially radiolucent, so as to minimize or reduce its interaction with the radiation beam. Such interactions can be a particular problem if the radiation is used for imaging. Alternatively, the mechanism 120 may be manufactured from non-radiolucent materials (such as metal), but positioned towards an end of the patient support 114 which does not fall within the path of the radiation beam during ordinary treatment (e.g. at the foot of the bed 116).

As will be clear from the description above, the attachment 122 may be any add-on device for a radiation head, such as a collimator or an electron applicator.

The steps of the attachment method can now be described. FIG. 1A shows a stage of the method in which the attachment 122 is positioned adjacent to the patient support 114. The gantry 110 is at an angle of rotation such that the radiation head 112 does not obstruct movement of the patient support 114. In the illustrated example, the gantry 110 is in an upright position such that the radiation head 112 is at its highest point.

The attachment 122 is positioned vertically below the engagement mechanism 120. In an embodiment, this positioning is achieved automatically so as to avoid heavy manual lifting. For example, the attachment 122 may be put into place by a conveyor belt, or by a lift through the floor cavity, or by selection from a carousel incorporating multiple attachments.

Figure 1B:
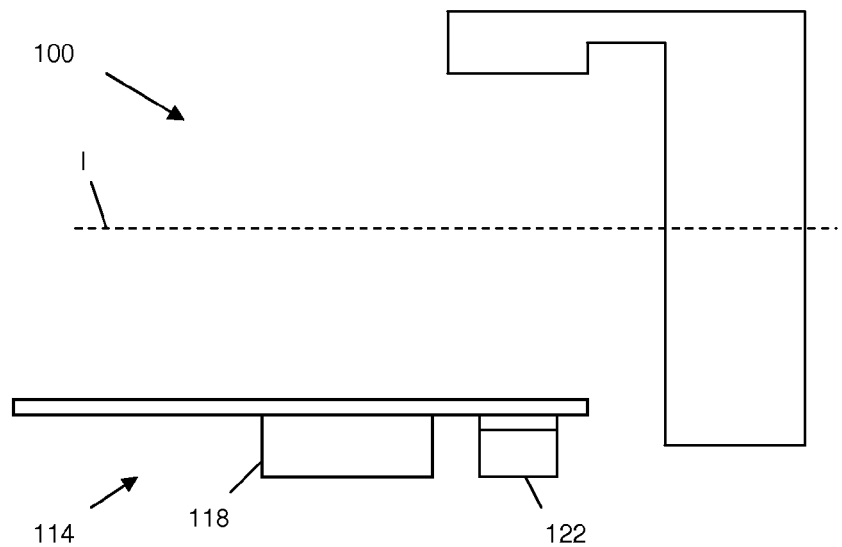

FIG. 1B shows the next stage of the method, in which the support mechanism 118 is controlled so as to lower the engagement mechanism 120 into engagement with the attachment 122. The bed 116 is also lowered by the action of the support mechanism 118. The mechanism 120 couples rigidly to the attachment 122.

Figure 1C:
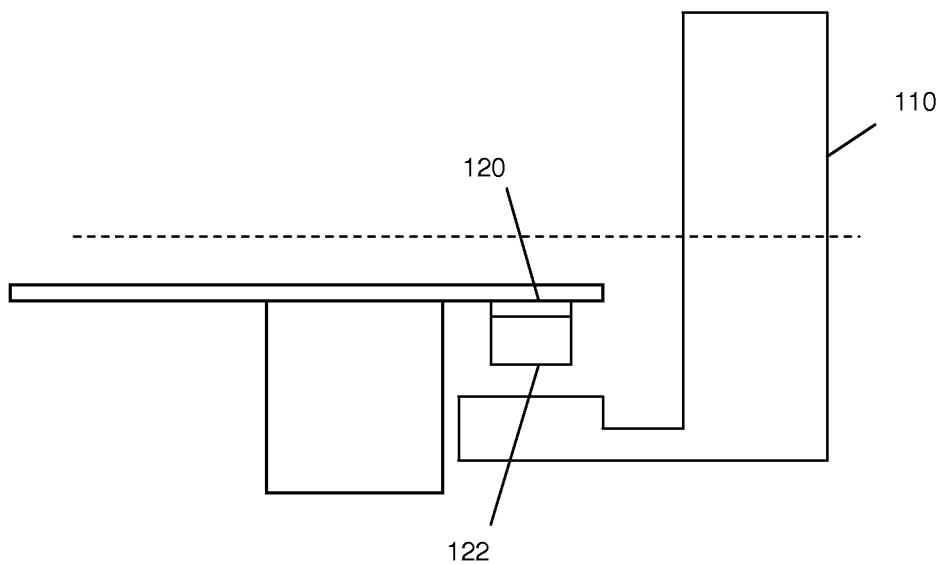

In FIG. 1C, the support mechanism 118 has been controlled to raise the bed 116 vertically, lifting the engagement mechanism 120 as well as the attachment 122 which is engaged with it. In addition, the gantry 110 is rotated such that the radiation head 112 lies beneath the attachment 122, possible due to the vertical lift provided by the support mechanism 118. In the illustrated embodiment this means that the radiation head 112 is at its lowest position at the bottom of the gantry 110.

At this stage it will be understood by those skilled in the art that the number of steps and their order could be changed from those illustrated without substantively affecting the operation of the invention. For example, in FIG. 1A the attachment 122 is shown directly below the engagement mechanism 120 and both are substantially in line with the radiation head 112. In alternative embodiments the attachment 122 and the engagement mechanism 120 may be at the foot of the bed 116, and out of line with the radiation head. Once the mechanism 120 is brought into engagement with the attachment 122, rotation and/or translation of the patient support 114 by the support mechanism 118 (e.g. 180 degrees of rotation) can bring the attachment into line with the radiation head 112. In this embodiment, the radiation head 112 may be put into its lower position before the rotation and/or translation of the patient support 114, provided there is sufficient clearance for the apparatus to move without collision.

Figure 1D:
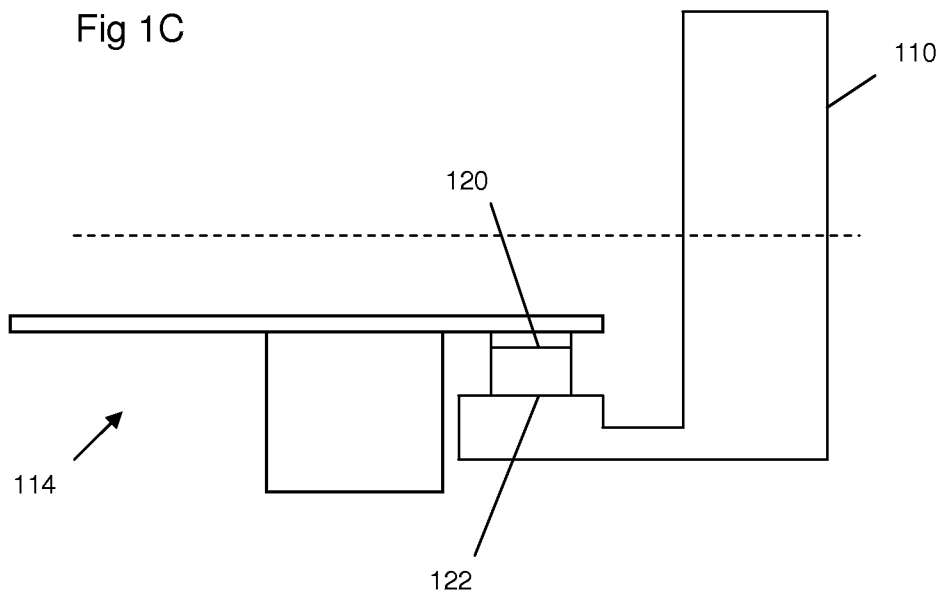

In FIG. 1D, the support mechanism 118 is controlled to lower the bed 116, the engagement mechanism 120 and the attachment 122, bringing the attachment into engagement with the radiation head 112. The attachment 122 is coupled to the radiation head 112, and decoupled from the engagement mechanism 120. Again, the mechanism for attaching the attachment 122 to the radiation head 112 will be familiar to those skilled in the art. It may be automatic (in that it can be controlled mechanically or electronically), or manually controlled.

Figure 1E:
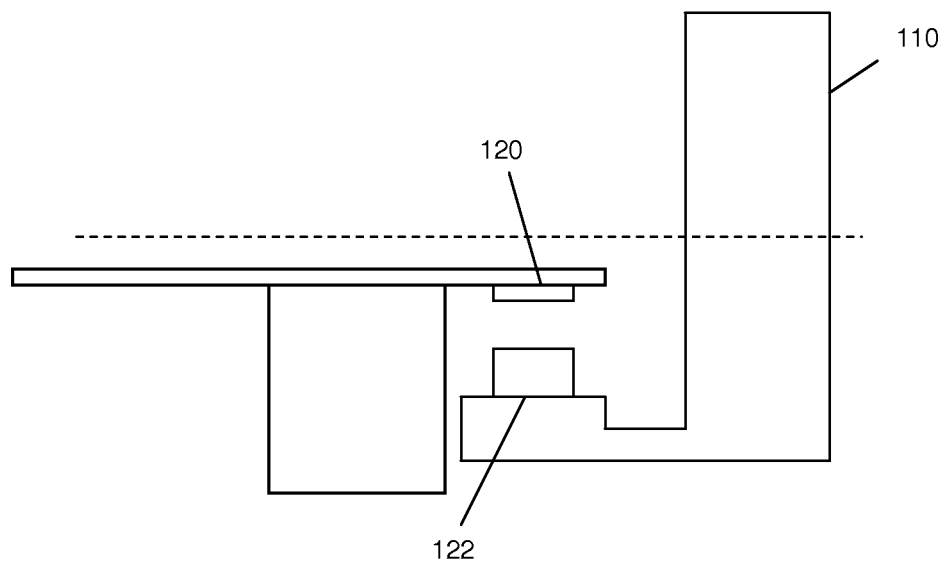
Figure 1F:
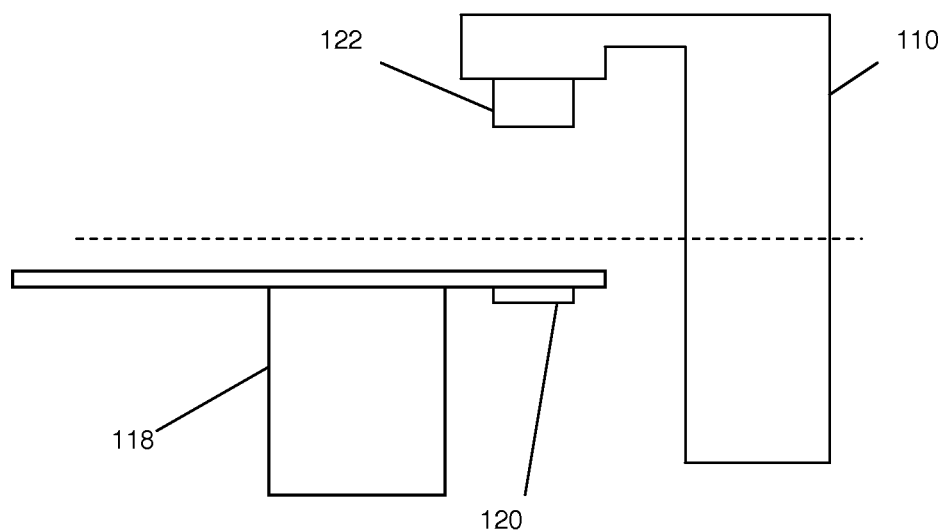
Figure 1G:
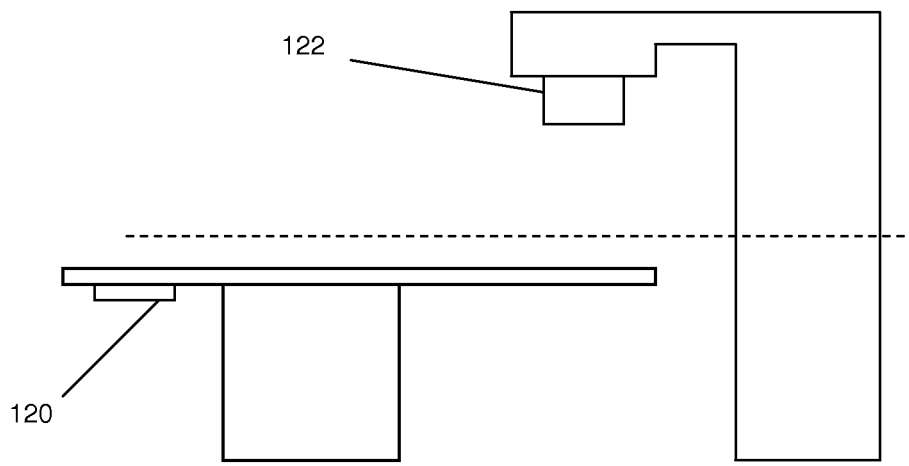

In FIG. 1E, the support mechanism 118 is controlled to raise the bed 116 and the engagement mechanism 120, for example, to a position suitable for supporting a patient undergoing therapy. In FIG. 1F the gantry 110 is shown at a new angle of rotation with the attachment 122 now fixed to the radiation head 112 (for example as might be used during operation of the system 100 for treatment). In embodiments of the present invention (particularly if the engagement mechanism 120 is not radiolucent), the patient support 114 may be rotated or moved such that the engagement mechanism 120 lies outside the radiation beam once the radiotherapy system 100 is in operation (FIG. 1G). For example, the engagement mechanism 120 may be positioned at what is conventionally the foot of the bed 116. Therefore a 180 degree rotation about a vertical axis positions the engagement mechanism away from the radiation head 112. With the radiation conventionally intersecting the patient support at the head of the bed 116 (i.e. the opposite end to the foot), the engagement mechanism 120 no longer interacts with the radiation produced by the radiation head 112 during treatment.

Although described in the context of a radiotherapy system, it will be apparent to those skilled in the art that the present invention is equally applicable to any system employing a radiation head and requiring attachments to be coupled to that radiation head. For example, the system may be used solely for imaging purposes.

The methods and apparatus set out above are described in the context of bringing an attachment into engagement with the radiation head 112. However, it will further be clear to those skilled in the art that the attachment may equally be brought into engagement with any other suitable connection point on the gantry 110. For example, an arm may extend from the gantry in order to support an imaging device or other attachment, and thus may provide a connection point in the same way that the radiation head 112 provides a connection point. The arm and gantry 110 can be manipulated in the same way as the radiation head 112 and gantry 110 are manipulated above, in order to bring the attachment into engagement with the arm. In these embodiments, the attachment may comprise light sources, X-ray detectors or sources, laser scanners, ultrasound or infrared sensors for patient motion or proximity measurements, video cameras or other sensors, detectors etc.

Embodiments of the present invention thus provide a system and a method for attaching peripheral devices (such as collimators, electron applicators or other devices) to a system such as a radiotherapy system or radiography system. By re-using the lifting mechanism of the patient support to lift the peripheral device vertically, the invention reduces the need for heavy manual lifting.

Those skilled in the art will appreciate that various amendments and alterations can be made to the embodiments described above without departing from the scope of the invention as defined in the claims appended hereto.

What is claimed is:

1. An apparatus, comprising:
   a rotatable gantry;
   a connection point mounted on the rotatable gantry;
   an attachment for attachment to the connection point;
   a patient support for supporting a patient, comprising an engagement mechanism for engagement with the attachment; and
   a control apparatus for controlling at least the patient support and the rotatable gantry, the control apparatus arranged to:
      bring the engagement mechanism into engagement with the attachment;
      raise the patient support and thus also the attachment;
      position the connection point beneath the attachment;
      lower the patient support and engage the attachment with the connection point; and
      disengage the engagement mechanism from the attachment.

2. The apparatus according to claim 1, wherein the patient support comprises a surface for supporting a patient, and one or more adjustment mechanisms for adjusting at least the height of the surface, the one or more adjustment mechanisms also adjusting the height of the engagement mechanism.

3. The apparatus according to claim 1, wherein the control apparatus is further arranged to:
   move the patient support so that the engagement mechanism lies outside the plane in which the connection point moves due to rotation of the gantry.

4. The apparatus according to claim 1, wherein the attachment comprises a collimator or an electron applicator.

5. The apparatus according to claim 1, wherein the connection point is arranged on an arm mounted on the rotatable gantry, the arm projecting away from the rotatable gantry in a direction along a rotation axis of the rotatable gantry.

6. The apparatus according to claim 1, wherein the apparatus is a radiotherapy or radiography apparatus.

7. The apparatus according to claim 6, wherein the connection point is arranged on a radiation head mounted on the rotatable gantry.

* * * * *